United States Patent [19]

Holtkamp

[11] Plant 4,551

[45] Jun. 17, 1980

[54] AFRICAN VIOLET PLANT

[75] Inventor: Reinhold Holtkamp, Isselburg, Fed. Rep. of Germany

[73] Assignee: Gessellschaftsvertrag uber die Erfindergemeainschaft "Optimara", Isselburg, Fed. Rep. of Germany

[21] Appl. No.: 15,826

[22] Filed: Feb. 27, 1979

[51] Int. Cl.[2] ..... A01H 5/00

[52] U.S. Cl. ..... Plt./69

[58] Field of Search ..... Plt./69

*Primary Examiner*—Robert E. Bagwill
*Assistant Examiner*—James R. Feyrer
*Attorney, Agent, or Firm*—Donald D. Jeffery

[57] ABSTRACT

An African violet known by the cultivar name North Dakota having up to ten flower stems, each carrying up to 10 or more single flowers generally white in color with blue-violet edges and centers, and vigorous growth habit, with the plant being in full flower after 9–10 weeks from potting.

1 Drawing Figure

1

The present invention comprises a new and distinct cultivar of African violet plant, botanically known as *Saintpaulia ionantha,* and hereinafter referred to by the cultivar name North Dakota.

The new cultivar was referred to during the breeding and selection process by the designation C 121/3-181/79, and is a product of a planned breeding program. North Dakota has white flowers with blue centers and edges, with up to 10 and more single flowers being carried on each stem. The growth is vigorous, and the leaves are medium green, velvety. These traits in combination were not present in previously available commercial cultivars.

The new cultivar was originated from a cross made in a controlled breeding program in Isselburg, Rhineland, Germany. The female, or seed parent was a cultivar designated XIX 4240 blue, unpatented. The male, or pollen parent was a cultivar designated X 32 blue-white Bie, likewise unpatented.

The new cultivar North Dakota was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of North Dakota which in combination distinguish this African violet as a new and distinct cultivar:

(1) White flowers having blue-violet edges and centers with flowers carried up to 10 on each stem; on older plants 15 or more flowers carried on each stem.

(2) 7–10 flower-stems with the first flash of flowers.

(3) Stems are upright and wiry.

(4) Vigorous grower, being in full bloom in 9–10 weeks after potting.

(5) Attractive medium green leaves, which are velvety and slightly hairy.

2

The accompanying photographic drawing shows a typical specimen plant of the new cultivar. The colors appearing in the photograph are as true as possible with color illustrations of this type.

In the following description, color references are made both to the Royal Horticultural Society color chart (RHS) and to the Horticultural Colour Chart (HCC) issued by Wilson Colour Ltd. The use of both of these references is to provide as much accuracy as possible regarding color values.

Botanical classification: *Saintpaulia ionantha,* Ramat. cv North Dakota.

Parentage:

*Male parent.*—X 32 blue-white Bie.

*Female parent.*—XIX 4240 blue.

Propagation: The new cultivar holds its distinguishing characteristics through successive propagations by leaf cuttings and by division of shoots.

Plant: From 9 cm. to 12 cm. tall when grown in pots, and approximately 25–35 cm. in diameter when fully grown.

Leaves:

*General form.*—Oval.

*Diameter.*—65–75 mm.

*Texture.*—Soft.

*Aspect.*—Velvety-shiny, edges slightly serrated.

*Veins.*—Well pronounced on underside.

*Color (upperside).*—HCC 0960/1 (spinach-green).

*Color (underside).*—HCC 000 658/2.

*Petiole.*—Strong, hairy, light green.

Flowers:

*Buds.*—Ball-shaped, just before opening 7–9 mm. in diameter.

*Sepals.*—5 in number, spear-shaped. Color: medium green, HCC 55/3. Calyx: seed bud grown together with receptacle. Aspect: funnel shaped. Peduncle: wiry, bent to the center, slightly hairy.

Individual flowers:

*Size.*—34–45 mm.

*Color.*—Upperside: base color, white RHS 155C; center and edges RHS 88 A Underside: base color, white RHS 155C; center and edges RHS 88 A.

*Borne.*—The flower stems are wire-like and upright and carry up to 10 and more single flowers.

*Shape.*—5 petals, 3 large, 2 smaller; the large are 20×17 mm.; the small 10×10 mm.

*Flowering time.*—8 weeks after potting the first flowers appear, 10 weeks to full bloom.

Reproductive organs:

*Stamens.*—2 in number.

*Anthers.*—4 anthers.

*Filaments.*—3–4 mm. long, light green-yellow in color.

*Styles*—7–9 mm. long, color similar to the color of petals, seed capsule is light green, hairy.

Roots: Well developed and branched out root system; white when young, turning brownish when older.

Disease resistance: No disease problems to date.

General observations: North Dakota is a vigorous, fast growing variety with up to 10 flower stems, and up to 10 and more individual flowers on each stem. The main color of the flower is white, with the center and edges being blue-violet. The plant is in full flower after 9–10 weeks cultivation from potting a well developed starter.

I claim:

1. A new and distinct cultivar of African violet, as shown and described, known by the cultivar name North Dakota and characterized by the combined features of up to ten flower stems, each carrying up to 10 or more single flowers generally white in color with blue-violet edgs and centers, and vigorous growth habit, with the plant being in full flower after 9–10 weeks from potting.

* * * * *

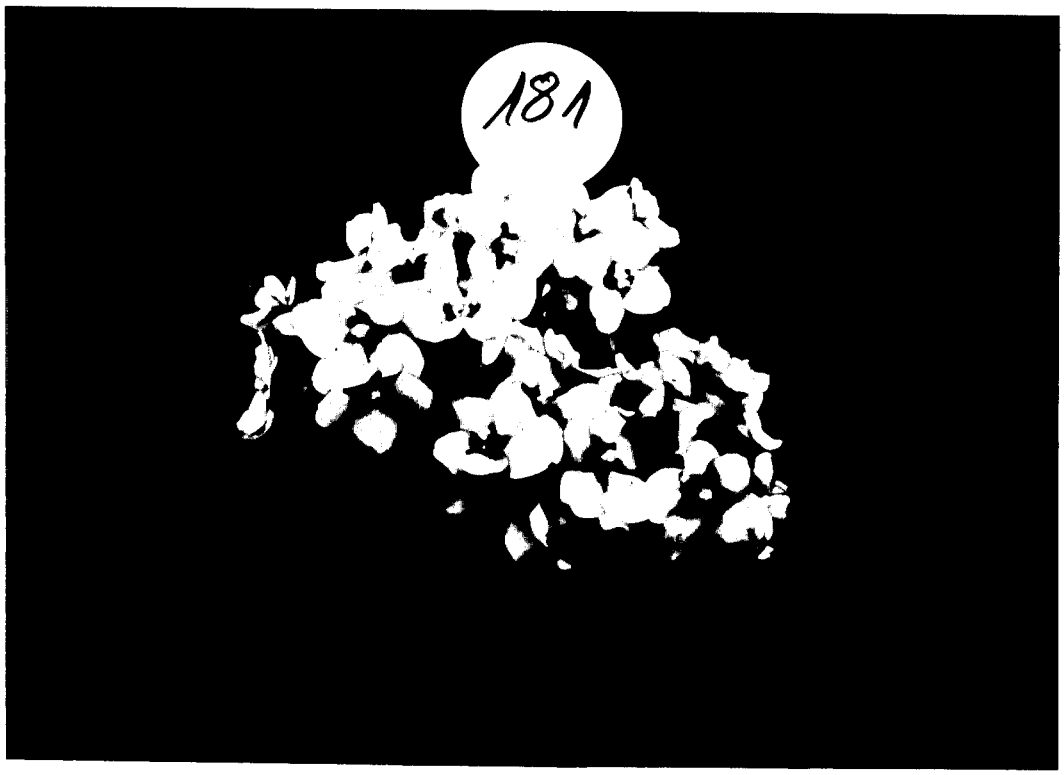
181